United States Patent [19]
Arai et al.

[11] 3,979,412
[45] Sept. 7, 1976

[54] PROCESS FOR PRODUCING 3-ANILINO-5-PYRAZOLONES

[75] Inventors: Atsuaki Arai, Minami-ashigara; Daijiro Nishio, Odawara; Mitsugu Tanaka, Minami-ashigara; Yoshikazu Fujita; Hisao Suzuki, both of Odawara, all of Japan

[73] Assignee: Fuji Photo Film Co., Ltd., Minami-ashigara, Japan

[22] Filed: Oct. 30, 1974

[21] Appl. No.: 519,310

[30] Foreign Application Priority Data
Oct. 30, 1973    Japan.............................. 48-121955

[52] U.S. Cl............................................. 260/310 A
[51] Int. Cl.² ...................................... C07D 231/52
[58] Field of Search ................................ 260/310 A

[56] References Cited
UNITED STATES PATENTS 3,798,234    3/1974    Meier et al. .................... 260/310 A

FOREIGN PATENTS OR APPLICATIONS 1,129,333    10/1968    United Kingdom............. 260/310 A
1,129,334    10/1968    United Kingdom............. 260/310 A
1,134,329    11/1968    United Kingdom............. 260/310 A Primary Examiner—Donald B. Moyer
Attorney, Agent, or Firm—Sughrue, Rothwell, Mion, Zinn & Macpeak

[57] ABSTRACT

A process for producing a 3-anilino-5-pyrazolone which comprises reacting a β-anilino-β-alkoxy-acrylate with a hydrazine in the presence of a compound having a pKa of about 8 up to about 14.

5 Claims, No Drawings

PROCESS FOR PRODUCING 3-ANILINO-5-PYRAZOLONES

BACKGROUND OF THE INVENTION

1. FIELD OF THE INVENTION

The present invention relates to an improved process for producing 3-anilino-5-pyrazolones.

2. DESCRIPTION OF THE PRIOR ART

3-Anilino-5-pyrazolones are useful compounds as intermediates for dyestuffs or as magenta color formers. Of the 3-anilino-5-pyrazolones, compounds having a substituent such as a halogen atom, an alkyl group or an alkoxy group in the 2-position of the 3-anilino group and a hydrophobic group containing 6 or more carbon atoms in the 3-anilino group are very useful as magenta color formers, because they have particularly excellent photographic properties.

Hitherto, many processes have been suggested in order to synthesize the 3-anilino-5-pyrazolones. However, these processes have the defects that either the process is complicated, the reaction yield is low or the starting materials are expensive, etc. Of these processes, the process described in British Pat. 1,129,333, namely, the process which comprises reacting β-anilino-β-alkoxyacrylates with hydrazines in the presence of an alkali metal alkoxide, is most effective. However, the yield of this process is not always high. Particularly, when this process is applied to the synthesis of pyrazolones having a hydrophobic group in the 3-anilino group, the desired 3-anilino-5-pyrazolones are hardly obtained or obtained in a very small amount.

SUMMARY OF THE INVENTION

Accordingly, one object of the present invention is to provide an improved process for producing 3-anilino-5-pyrazolones.

Another object is to provide a process for producing 3-anilino-5-pyrazolones easily in a very high yield.

A further object is to provide a process which can be applied to the synthesis of many kinds of 3-anilino-5-pyrazolones.

An even further object is to provide a process for easily producing 3-anilino-5-pyrazolones having a hydrophobic group in the 3-anilino group in a high yield.

These and other objects will be clear from the following descriptions.

These objects have been attained by the process of this invention for producing 3-anilino-5-pyrazolones which comprises reacting a β-anilino-β-alkoxyacrylate with a hydrazine using a compound having a pKa of about 8 up to about 14.

DETAILED DESCRIPTION OF THE INVENTION

The process of the present invention is particularly useful in the case of producing 3-anilino-5-pyrazolones represented by the general formula (I),

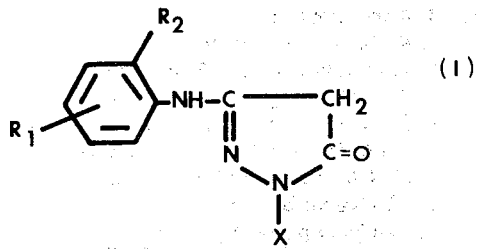

(I)

wherein $R_1$ represents an acylamino group, an alkylsulfamoyl group, an arylsulfamoyl group or an alkoxycarbonyl group; $R_2$ represents a halogen atom, an alkyl group or an alkoxy group, and X represents an aryl group.

In the general formula (I) it is preferred that $R_1$ contains 6 or more carbon atoms and preferably 8 to 26 carbon atoms. The alkyl moiety or the aryl moiety for the above listed groups for $R_1$ can be substituted.

Suitable acylamino groups, alkylsulfamoyl groups, arylsulfamoyl groups and alkoxycarbonyl groups represented by $R_1$ in the general formula (I) are acylamino groups such as hexanoylamino, octanoylamino, decanoylamino, hexadecanoylamino, octadecanoylamino, 2,4-di-tert-pentylphenoxyacetamido, 2-(2,4-di-tert-pentylphenoxy)butyramido, 4-(3-pentadecylphenoxy)butyramido, etc., alkylsulfamoyl groups such as cyclohexylsulfamoyl, dodecylsulfamoyl, 1,1-dimethylhexadecylsulfamoyl, 3-(2,4-di-tert-pentylphenoxy)propylsulfamoyl, 4(3-pentadecylphenoxy)butylsulfamoyl, 2-(dodecylsuccinimido)ethylsulfamoyl, N-methyl-N-octadecylsulfamoyl, etc., arylsulfamoyl groups such as phenylsulfamoyl, 4-methylphenylsulfamoyl, 4-dodecylphenylsulfamoyl, and alkoxycarbonyl groups such as hexyloxycarbonyl, dodecyloxycarbonyl, tetradecyloxycarbonyl, 2-(2,4-di-tert-pentylphenoxy)ethoxycarbonyl, 4-(2,4-di-tert-pentylphenoxy)butoxycarbonyl, 2-(3-tert-butyl-4-hydroxyphenoxy)tetradecyloxycarbonyl, 2-dodecyloxycarbonylethoxycarbonyl, etc.

Suitable halogen atoms represented by $R_2$ in the general formula (I) include fluorine, chlorine and bromine, and suitable alkyl groups and alkoxy groups represented by $R_2$ include those having 1 to 8 carbon atoms. Suitable examples of alkyl groups and alkoxy groups for $R_2$ are alkyl groups such as methyl, ethyl, butyl, hexyl, etc., and alkoxy groups such as methoxy, ethoxy, butoxy, hexyloxy, etc. A chlorine atom, alkyl groups having 1 to 4 carbon atoms and alkoxy groups having 1 to 4 carbon atoms are particularly preferred as $R_2$.

Suitable aryl groups represented by X in the general formula (I) include substituted or unsubstituted phenyl groups.

Preferred substituents of the alkyl moiety of $R_1$ include halogen atoms (such as chlorine, bromine, fluorine, etc.), alkoxy groups (such as methoxy, ethoxy, butoxy, octyloxy, etc.), acyl groups (such as acetyl, propionyl, etc.), alkoxycarbonyl groups (such as methoxycarbonyl, ethoxycarbonyl, hexadecyloxycarbonyl, etc.), a carboxyl group, a sulfo group, a nitro group, amino groups, acylamino groups (such as acetamido, butyramido, 2-(2,4-di-tert-pentylphenoxy(butyramido, benzamido, etc.), sulfonamido groups (such as methylsulfonamido, phenylsulfonamido, etc.), ureido groups (such as methylureido, phenylureido, etc.) and a cyano group. Preferred substituents of the aryl moiety of $R_1$ and the phenyl group of X include halogen atoms (such as chlorine, bromine, fluorine, etc.), alkyl groups (such as methyl, ethyl, butyl, octyl, trifluoromethyl, etc.), alkoxy groups (such as methoxy, ethoxy, butoxy, octyloxy, etc.), acyl groups (such as acetyl, propionyl, etc.), alkoxycarbonyl groups (such as methoxycarbonyl, ethoxycarbonyl, hexadecyloxycarbonyl, etc.), a carboxyl group, a sulfo group, a nitro group, amino groups, acylamino groups (such as acetamido, butyramido, 2-(2,4-di-tert-pentylphenoxy)- butyramido, benzamido, etc.), sulfonamido groups (such as methylsulfonamido, phenylsulfonamido, etc.), ureido groups (such as methylureido, phenylureido, etc.) and a cyano group.

According to the process of the present invention, the 3-anilino-5-pyrazolones represented by the general formula (I) can be produced by reacting β-anilino-β-alkoxyacrylates represented by the general formula (II) with aryl hydrazines represented by the general formula (III).

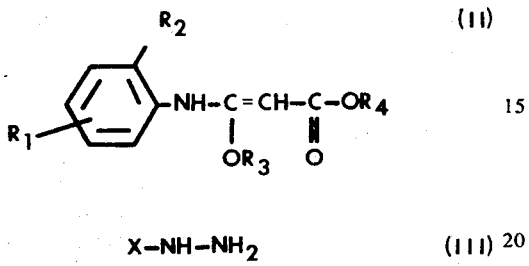

$$X-NH-NH_2 \quad (III)$$

In the general formulas (II) and (III), $R_1$, $R_2$ and X represent the same meanings as in general formula (I), and $R_3$ and $R_4$ each represents an alkyl group which may be the same or different from each other. Suitable alkyl groups represented by $R_3$ and $R_4$ in the formula (II) include those having 1 to 8 carbon atoms, for example, alkyl groups such as methyl, ethyl, butyl, hexyl, etc. Alkyl groups having 1 to 4 carbon atoms are particularly preferred for $R_3$ and $R_4$.

The β-anilino-β-alkoxyacrylates used in the present invention can be produced by processes described in British Pat. No. 1,129,334, French Pat. No. 1,469,360, U.S. Pat. No. 3,798,234 and Japanese Pat. Application No. 87726/1973.

Typical examples of β-anilino-β-alkoxyacrylates include the following compounds.

1. β-(2-Chloro-5-tetradecanoylaminoanilino)-β-ethoxyacrylic acid ethyl ester
2. β-(2-Methoxy-5-tetradecanoylaminoanilino)-β-ethoxyacrylic acid ethyl ester
3. β-(2-Chloro-5-octadecanoylaminoanilino)-β-methoxyacrylic acid methyl ester
4. β-(2-Methoxy-5-decanoylaminoanilino)-β-ethoxyacrylic acid ethyl ester
5. β-(2-Chloro-5-hexadecanoylaminoanilino)-β-ethoxyacrylic acid ethyl ester
6. β-{2-Methoxy-5-[2-(2,4-di-tert-pentylphenoxy)butyramino]anilino}-β-methoxyacrylic acid butyl ester
7. β-(2-Chloro-4-tetradecylsulfamoylanilino)-β-ethoxyacrylic acid ethyl ester
8. β-(2-Chloro-5-tetradecylsulfamoylanilino)-β-ethoxyacrylic acid ethyl ester
9. β-(2-Chloro-5-dodecylsulfamoylanilino)-β-ethoxyacrylic acid ethyl ester
10. β-[2-Chloro-5-(1,1-dimethylhexadecylsulfamoyl)anilino]-β-ethoxyacrylic acid ethyl ester
11. β-(2-Octyloxy-5-cyclohexylsulfamoylanilino)-β-ethoxyacrylic acid ethyl ester
12. β-{2-Chloro-5-[3-(2,4-di-tert-pentyl)phenoxypropylsulfamoyl]anilino}-β-ethoxyacrylic acid methyl ester
13. β-{2-Chloro-5-[3-(3-pentadecylphenoxy)propylsulfamoyl]anilino}-β-ethoxyacrylic acid ethyl ester
14. β-{2-Chloro-5-[4-(3-pentadecylphenoxy)butylsulfamoyl]anilino}-β-ethoxyacrylic acid ethyl ester
15. β-{2-Chloro-5-[2-dodecylsuccinimide)ethylsulfamoyl]anilino}-β-ethoxyacrylic acid ethyl ester
16. β-{2-Chloro-4-[2-(3-tert-butyl-4-hydroxyphenoxy)tetradecylsulfamoyl]anilino}-β-ethoxyacrylic acid ethyl ester
17. β-{2-Chloro-5-[N-(2-cyanoethyl)-N-hexadecylsulfamoyl]anilino}-β-ethoxyacrylic acid ethyl ester
18. β-{2,5-Dichloro-4-[3-(2,4-di-tert-pentylphenoxy)propylsylfamoyl]anilino}-β-ethoxyacrylic acid ethyl ester
19. β-{2-Methoxy-5-[3-(2,4-di-tert-pentylphenoxy)propylsulfamoyl]anilino}-β-ethoxyacrylic acid ethyl ester
20. β-(2-Methoxy-5-tetradecylsulfamoylanilino)-β-ethoxyacrylic acid ethyl ester
21. β-[2-Chloro-5-(N-methyl-N-octadecylsulfamoyl)anilino]-β-ethoxyacrylic acid ethyl ester
22. β-{[2-Chloro-5-(4-dodecyl)phenylsulfamoyl]anilino}-β-ethoxyacrylic acid ethyl ester
23. β-(2-Methyl-5-dodecylsulfamoylanilino)-β-ethoxyacrylic acid methyl ester
24. β-{2-Chloro-5-[2-(N-butylhexadecylamido)ethylsulfamoyl]anilino}-β-ethoxyacrylic acid ethyl ester
25. β-(2,5-Dichloro-4-cyclohexylsulfamoylanilino)-β-ethoxyacrylic acid ethyl ester
26. β-(2-Chloro-5-tetradecyloxycarbonylanilino)-β-ethoxyacrylic acid ethyl ester
27. β-(2-Methyl-5-tetradecyloxycarbonylanilino)-β-ethoxyacrylic acid ethyl ester
28. β-{2-Methoxy-5-[2-(2,4-di-tert-pentylphenoxy)ethoxycarbonyl]anilino}-β-ethoxyacrylic acid ethyl ester
29. β-{2-Chloro-5-[2-(2-dodecylsuccinimido)ethoxycarbonyl]anilino}-β-ethoxyacrylic acid ethyl ester
30. β-[2-Chloro-5-(2-butoxytetradecyloxycarbonyl)anilino]-β-ethoxyacrylic acid ethyl ester
31. β-{2-Methyl-5-[4-(2,4-di-tert-pentylphenoxy)butoxycarbonyl]anilino}-β-ethoxyacrylic acid ethyl ester
32. β-{2-Chloro-5-[2-(3-pentadecylphenoxy)ethoxycarbonyl]anilino}-β-ethoxyacrylic acid ethyl ester
33. β-{2-Chloro-5-[2-(3-tert-butyl-4-hydroxyphenoxy)tetradecyloxycarbonyl]anilino}-β-ethoxyacrylic acid ethyl ester
34. β-[2-Methoxy-5-(2-hexyldecyloxycarbonyl)anilino]-βethoxyacrylic acid ethyl ester
35. β-[2-Chloro-4-(2-dodecyloxycarbonylethoxycarbonyl)anilino]β-ethoxyacrylic acid ethyl ester
36. β-[(2-Methoxy-5-tetradecyloxycarbonylmethoxycarbonyl)anilino]-β-ethoxyacrylic acid ethyl ester The hydrazines and, particularly, aryl hydrazines used in the present invention can be produced using known processes.

Typical examples of the hydrazines include the following compounds.

1. Phenylhydrazine
2. 2-Chlorophenylhydrazine
3. 4-Chlorophenylhydrazine
4. 4-Bromophenylhydrazine
5. 4-Fluorophenylhydrazine
6. 2,5-Dichlorophenylhydrazine
7. 2,6-Dichlorophenylhydrazine
8. 3,5-Dibromophenylhydrazine
9. 2,4,6-Trichlorophenylhydrazine
10. 2,4,6-Tribromophenylhydrazine
11. 2-Cyanophenylhydrazine
12. 4-Cyanophenylhydrazine 13. 3-Nitrophenylhydrazine
14. 4-Aminophenylhydrazine
15. 4-Methylaminophenylhydrazine
16. 4-Acetamidophenylhydrazine
17. 4-[2-(2,4-Di-tert-pentylphenoxy)butyramido]-phenylhydrazine
18. 2,6-Dimethylphenylhydrazine
19. 2,6-Diethylphenylhydrazine
20. 2-Trifluoromethylphenylhydrazine
21. 4-Methoxyphenylhydrazine
22. 2-Ethoxyphenylhydrazine
23. 4-Phenylphenylhydrazine
24. 4-Phenoxyphenylhydrazine
25. 4-Butylphenylhydrazine
26. 4-(N-Methylbenzamido)phenylhydrazine
27. 3-(N,N-Diethylcarbamoyl)phenylhydrazine
28. 4-(N-methylphenylsulfonamido)phenylhydrazine
29. 4-Methylureidophenylhydrazine
30. 3-Acetylphenylhydrazine
31. 2-Methyl-5-nitrophenylhydrazine
32. 2-Chloro-5-cyanophenylhydrazine
33. 2-Methyl-5-chlorophenylhydrazine
34. 2,6-Dichloro-4-methylphenylhydrazine
35. 2,6-Dichloro-4-methoxyphenylhydrazine
36. 2,4-Dichloro-6-methylphenylhydrazine
37. 2-Chloro-4,6-dimethylphenylhydrazine
38. 2,6-Dichloro-4-nitrophenylhydrazine
39. 2,4,6-Trimethyl-3-nitrophenylhydrazine
40. 2,4,6-Trimethyl-3-acetamidophenylhydrazine
41. 2,5-Dicarboxyphenylhydrazine
42. 4-Ethoxycarbonylphenylhydrazine
43. 2,6-Dichloro-4-tetradecyloxycarbonylphenylhydrazine
44. 4-(N,N-Dimethylsulfamoyl)phenylhydrazine
45. 3-Sulfo-4-phenoxyphenylhydrazine
46. 2-Methoxy-5-methyl-3,4,6-trichlorophenylhydrazine
47. 3-Dimethylamino-4-bromophenylhydrazine
48. Naphthylhydrazine
49. Butylhydrazine
50. Cyclohexylhydrazine
51. 2-Benzothiazolylhydrazine Examples of the compounds having a pKa of about 8 up to about 14 which can be used in the present invention include phenol, o-, m- and p-chlorophenol; o-, m- and p-cresol; o-, m- and p-fluorophenol; o-, m- p-bromophenol; 2,3-, 2,4-, 2,5-, 2,6-, 3,4- and 3,5-dimethylphenol; 2,3,5- and 2,4,6-trimethyl-phenol; o-, m- and p-methoxyphenol; tert-butylphenol; hydroquinone; catechol; resorcinol; methylhydroquinone; tertbutyhydroquinone; n-octylhydroquinone; 2,5-di-tert-butylhydroquinone; naphthol and boric acid. Particularly, compounds having a pKa of 9 to 11 such as phenol, o-, m- or p-cresol, etc., are preferred.

Ratios of each component used for the reaction can vary over a broad range. However, in general, good results can be obtained when the hydrazine is used in the amount of about 0.5 to 2.5 mols, preferably 1 to 1.3 mols, per mol of the β-anilino-β-alkoxyacrylate and the compound having a pKa of about 8 up to about 14 is used in the amount of about 0.1 to 10 mols, preferably 0.5 to 5 mols, per mol of the β-anilino-β-alkoxyacrylate.

The reaction of the β-anilino-β-alkoxyacrylates with the hydrazines is generally carried out in the absence of solvents, However, if desired, inert solvents can be used. Suitable preferred examples of inert solvents are those which can dissolve the starting materials and have a boiling point above about 50°C. Specific examples of such solvents include methanol, ethanol, propanol, butanol, benzene, chlorobenzene, xylene, ethylene glycol monomethyl ether, ethylene glycol monoethyl ether, tetrahydrofuran and dioxane. In general, the reaction is carried out at a temperature of about 50° to 200°C. Although the reaction temperature will vary according to kind of starting material, a temperature in a range of 80° to 120°C is generally effective. It is preferred that the reaction be carried out at a reduced pressure, generally at a pressure of about 20 to 100 mmHg, in an inert gas atmosphere such as an atmosphere of nitrogen gas, argon gas, etc., in order to prevent coloration of the reaction product.

It has been understood that the alkoxy group in the β-position is replaced by a hydrazino group to form a β-anilinoβ-hydrazinoacrylate when a β-anilino-β-alkoxyacrylate is reacted with a hydrazine in the presence of a compound having a pKa of about 8 up to about 14 according to the present invention. For example, compounds represented by the general formula (IV) are formed from acrylates represented by the general formula (II) and hydrazines represented by the general frmula (III),

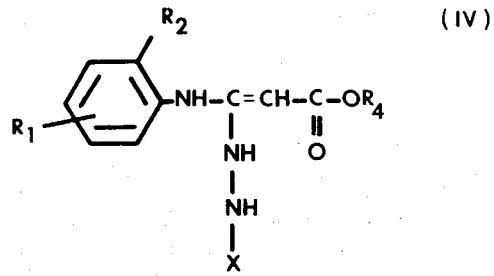

wherein in the general formula (IV), $R_1$, $R_2$, $R_4$ and X have the same meanings as in the general formulae (II) and (III).

The β-anilino-β-hydrazino-acrylates, for example, the compounds represented by the general formula (IV) easily undergo a ring closure reaction to form 3-anilino-5-pyrazolones, for example, the compounds represented by the general formula (I) in a high yield by using a strong alkali, for example, an alkali metal or alkaline earth metal hydroxide such as sodium hydroxide, potassium hydroxide or barium hydroxide, or an alkali metal alkoxide such as sodium ethoxide or potassium butoxide. This reaction can be carried out at about −10° to 50°C, preferably 0° to 30°C in the presence of an inert solvent, for example, in one of the above described inert solvents. A suitable amount of the strong alkali can range from about 0.5 to 10 mols, preferably 1 to 2 mols, per mole of the β-anilino-β-hydrazino-acrylates. The reaction can be carried out at normal pressure and preferably is conducted in an inert atmosphere such as a nitrogen, argon, etc., atmosphere.

In producing 3-anilino-5-pyrazolones according to the present invention, the ring closure reaction can be carried out after separating the resulting β-anilino-β-hydrazinoacrylates as intermediates or carried out continuously without separation. If the ring closure reaction is carried out after separation of the β-anilino-β-hydrazinoacrylates and purification thereof, there is an advantage that pure 3-anilino-5-pyrazolones which do not require purification at the final step can be obtained, because by-products do not form in the ring closure reaction.

An important advantage of the present invention is that 3-anilino-5-pyrazolones having a hydrophobic group in the 3-anilino group which are difficult or impossible to produce using known methods can be obtained easily in a high yield. This is because the compounds having a pKa of about 8 up to about 14 used in this invention have the function of inhibiting complicated side-reactions to accelerate the formation of β-anilino-βhydrazinoacrylates. In producing 3-anilino-5-pyrazolones having a hydrophobic group in the 3-anilino group, there is a process wherein 3-anilino-5-pyrazolones are produced first and a hydrophobic group is then introduced thereto. For example, 1-phenyl-3-(2-chloro-5-tetradecanoylaminoanilino)-5-pyrazolone can be produced by reacting β-alkoxy-β-(2-chloro-5-nitroanilino)acrylic acid ethyl ester with phenylhydrazine, reducing the resulting 1-phenyl-3-(2-chloro-5-nitroanilino)-5-pyrazolone, and reacting the resulting 1-phenyl-3-(2-chloro-5-aminoanilino)-5-pyrazolone with tetradecanoic acid after sufficient purification. However, this process is very inferior to the process of the present invention because of the complicated reaction steps and of the low yield.

The present invention will be illustrated in the following in greater detail by reference to examples. Unless otherwise indicated, all parts, percents, ratios and the like are by weight.

EXAMPLE 1

9.8 g of β-(2-chloro-5-tetradecanoylaminoanilino)-β-ethoxyacrylic acid ethyl ester, 6.3 g of 2,4,6-trichlorophenylhydrazine and 10.0 g of phenol (pKa value: 9.998) were heated for 6 hours at 80°C under a reduced pressure of 30 mmHg. After adding 40 ml of methanol and 1.6 g of sodium hydroxide, the reaction mixture was refluxed for 10 minutes in a water bath. Then the reaction mixture was poured into about 100 ml of ice water. The reaction mixture was extracted twice using 30 ml of chloroform for each extraction, and the extract was washed 3 times each with 50 ml of a 10% aqueous solution of sodium hydroxide, washed twice each with 60 ml of water and dried using anhydrous sodium sulfate. After removing the chloroform by distillation, the residue was determined by gel-permeation chromatography. Thus, it was confirmed that the residue contained 80% of 1-(2,4,6-trichlorophenyl)-3-(2-chloro-5-tetradecanoylaminoanilino)-5-pyrazolone. The residue was purified using silica gel chromatography (solvent: chloroform: ethyl acetate = 10 : 1 (volume)) to obtain 8.6 g of the desired product (yield: 70%). The melting point thereof after recrystallization from a mixed solvent of ethyl acetate-n-hexane (volume ratio: 1 : 1) was 92°-96°C.

COMPARISON EXAMPLE 1

The same procedure as described in Example 1 was carried out but 2,4,6-trichlorophenol (pKa value: 6.41) which was not within pKa range of the present invention was used instead of phenol. When measured by gel-permeation chromatography, the content of the desired compound was 45%.

EXAMPLE 2

The same procedures as described in Example 1 were carried out but o-cresol (pKa value: 10.287) was used instead of phenol. When measured by gel permeation chromatography, the content of the desired compound was 85%.

EXAMPLE 3

1-(2,6-Dichloro-4-methoxy)-3-{2-chloro-5-[2-(2,4-ditert-pentylphenoxy)butyramido]anilino}-5-pyrazolone was produced in the same manner as described in Example 1 but 50 g of β- 2-chloro-5-[2-(2,4-di-tert-pentylphenoxy)butyramido]anilino -β-ethoxyacrylic acid ethyl ester, 20 g of 2,6-dichloro-4-methoxyphenylhydrazine and 30 g of o-cresol were used. The melting point thereof after recrystallization from ethanol was 176° – 177°C.

EXAMPLE 4

1-(2,4,6-Trichlorophenyl)-3-{2-chloro-5-[3-(2,4-ditert-pentylphenoxy)propylsulfamoyl]anilino}-5-pyrazolone was produced in the same manner as described in Example 1 but 45 g of β-{2-chloro-5-[3-(2,4-di-tert-pentylphenoxy)propylsulfamoyl]anilino}-β-methoxyacrylic acid ethyl ester, 20 g of 2,4,6-trichlorophenylhydrazine and 30 g of phenol were used. The melting point thereof after recrystallization from ethanol was 173° – 175°C.

EXAMPLE 5

1-(2,4,6-Trichlorophenyl)-3-(2-methoxy-5-tetradecyloxycarbonylanilino)-5-pyrazolone was produced in the same manner as described in Example 1 but 40 g of β-(2-methoxy-5-tetradecyloxycarbonylanilino)-β-ethoxyacrylic acid ethyl ester, 20 g of 2,4,6-trichlorophenylhydrazine and 30 g of phenol were used. The melting point thereof after recrystallization from methanol was 100° – 112°C.

While the invention has been described in detail and with reference to specific embodiments thereof, it will be apparent to one skilled in the art that various changes and modifications can be made therein without departing from the spirit and scope thereof.

What is claimed is:

1. In a process wherein a β-anilino -β-alkoxyacrylate is reacted with a hydrazine in an amount of 0.5 to 2.5 moles per mole of said β-anilino-β-alkoxyacrylate to produce a 3-anilino-5-pyrazolone, the improvement comprising carrying out said reaction in the presence of 0.1 to 10 moles per mole of said β-anilino-β-alkoxyacrylate of a compound having a pKa of 8 up to 14, said compound selected from the group consisting of phenol, o-chlorophenol, m-chlorophenol, p-chlorophenol, o-cresol, m-cresol, p-cresol, o-fluorophenol, m-fluorophenol, p-fluorophenol, o-bromophenol, m-bromophenol, p-bromophenol, 2,3-dimethylphenol, 2,4-dimethylphenol, 2,5-dimethylphenol, 2,6-dimethylphenol, 3,4-dimethylphenol, 3,5-dimethylphenol, 2,3,5-trimethylphenol, 2,4,6-trimethylphenol, o-methoxyphenol, m-methoxyphenol, p-methoxyphenol, tertbutylphenol, hydroquinone, catechol, resorcinol, methylhydroquinone, tertbutylhydroquinone, n-octylhydroquinone, 2,5-ditert-butylhydroquinone, naphthol, boric acid and mixtures thereof.

2. The process of claim 1, wherein the reacting is at a temperature of 50° to 200°C under a reduced pressure of 20 to 100 mmHg and in an inert gas atmosphere.

3. The proess of claim 1, wherein said β-anilino-β-alkoxyacrylate is represented by the formula (I),

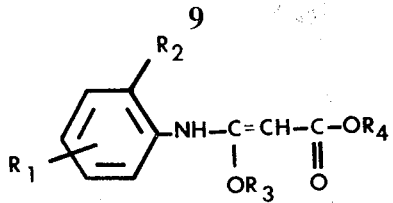

(I)

wherein R₁ represents an acylamino group selected from the group consisting of hexanoylamino, octanoylamino, decanoylamino, hexadecanoylamino, octadecanoylamino, 2,4-di-tert-pentylphenoxyacetamido, 2-(2,4-di-tert-pentylphenoxy)buyramido, and 4-(3-pentadecylphenoxy)-butyramido, an alkylsulfamoyl group selected from the group consisting of cyclohexylsufamoyl, dodecylsulfamoyl, 1,1-di-methyl-hexadecylsufamoyl, 3-(2,4-di-tert-pentylphenoxy) propylsulfamoyl, 4-(3-pentadecylphenoxy) butylsulfamoyl, 2-(dodecylsuccinimido) ethylsulfamoyl, and N-methyl-N-octadecylsulfamoyl, an arylsulfamoyl group selected from the group consisting of phenylsulfamoyl, 4-methylphenylsulfamoyl and 4-dodecylphenylsulfamoyl, or, an alkoxycarbonyl group selected from the group consisting of hexyloxycarbonyl, dodecyloxycarbonyl, tetradecyloxycarbonyl, 2-(2,4-di-tert-pentylphenoxy)ethoxycarbonyl, 4-(2,4-di-tertpentylphenoxy)-butoxycarbonyl, 2-(3-tert-butyl-4-hydroxyphenoxy) tetradecyloxycarbonyl, and 2-dodecyloxycarbonylethoxycarbonyl and R₂ represents a halogen atom, an alkyl group or an alkoxy group; and R₃ and R₄ each represents an alkyl group; and wherein said hydrazine is represented by the formula (II)

$$X - NH - NH_2 \qquad (II)$$

wherein X represents an aryl group.

4. The process of claim 3 wherein said halogen atom is fluorine, chlorine or bromine; said alkyl group has 1 to 8 carbon atoms and said alkoxy group has 1 to 8 carbon atoms.

5. The process of claim 3 wherein X is a substituted or unsubstituted phenol group.

* * * * *